United States Patent
Grisez et al.

(10) Patent No.: US 7,939,088 B2
(45) Date of Patent: May 10, 2011

(54) STREPTOCOCCUS PHOCAE VACCINE

(75) Inventors: Luc Grisez, Boxmeer (NL); Ruud Philip Antoon Maria Segers, Boxmeer (NL); Chow Yong Ng, Singapore (SG)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 12/355,273

(22) Filed: Jan. 16, 2009

(65) Prior Publication Data

US 2009/0130142 A1 May 21, 2009

Related U.S. Application Data

(62) Division of application No. 10/580,574, filed as application No. PCT/EP2004/053201 on Dec. 1, 2004, now abandoned.

(30) Foreign Application Priority Data

Dec. 3, 2003 (EP) .................................. 03104529

(51) Int. Cl.
*A61K 39/09* (2006.01)
*A01K 63/00* (2006.01)

(52) U.S. Cl. .................. 424/244.1; 424/93.44

(58) Field of Classification Search ................ 424/244.1
See application file for complete search history.

(56) References Cited

U.S. PATENT DOCUMENTS 6,379,677 B1 4/2002 Klesius et al.
6,518,252 B2 * 2/2003 Wooley et al. .................. 514/29

OTHER PUBLICATIONS

Mata et al Applied and Environmental Microbiology May 2004 pp. 3183-3187.*
Henton et al (Tydskr. S.Aft.vet.Ver.(1999), 70(2):98-99).*
Skaar et al International Journal of Systematic Bateriology Oct. 1994 pp. 646-650.*
Eldar, A. et al: "Development and efficacy of a vaccine against *Streptococcus iniae* infection in farmed rainbow . . . " Veterinary Immunology and Immunopathology 56:175-183 (1997).
Skaar, I. et al: "*Streptococcus phocae* sp. nov., a New Species Isolated from Clinical Specimens from Seals" Int'l J. of Systematic Bacteriology,44(4):646-650 (Oct. 1994).
Newman, S. "Bacterial Vaccines for Fish" Annual Rev. of Fish Diseases, 3:145-185 (1993).

* cited by examiner

*Primary Examiner* — Robert A Zeman
*Assistant Examiner* — Nina A Archie
(74) *Attorney, Agent, or Firm* — William M. Blackstone

(57) ABSTRACT

The present invention relates to the use of bacteria of the species *Streptococcus phocae* for the manufacture of a vaccine, to methods for the production of such vaccines, to bacteria of the species *Streptococcus phocae* for use in a vaccine and to methods for the combating of *Streptococcus phocae* infection in fish.

8 Claims, 3 Drawing Sheets

STREPTOCOCCUS PHOCAE VACCINE

PRIORITY CLAIM TO RELATED PATENT APPLICATIONS

Figure 1:
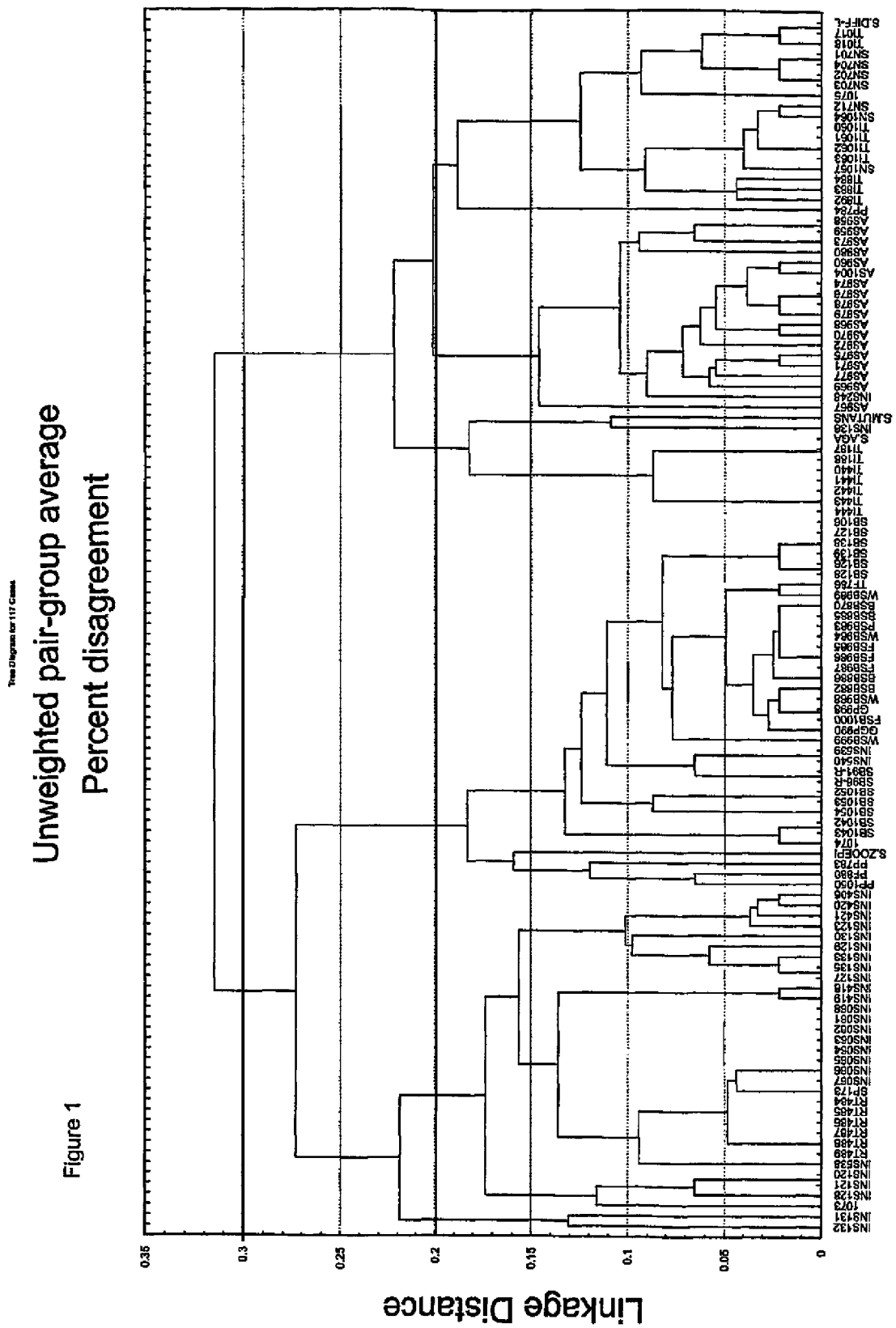

This patent claims priority under 35 U.S.C. §121 as a divisional of U.S. patent application Ser. No. 10/580,574 (filed May 25, 2006) now abandoned, which, in turn, claims priority under 35 USC §371 as a national phase of Intl Patent Appl. No. PCT/EP2004/053201 (filed Dec. 1, 2004; and published on Jun. 16, 2005 as Intl Publ. No. WO 2005/053716), which, in turn, claims priority to European Patent Appl. No. 03104529.7 (filed Dec. 3, 2003). The entire texts of the above-referenced patent applications are incorporated by reference into this application.

The present invention relates to the use of bacteria of the species *Streptococcus phocae* for the manufacture of a vaccine, to methods for the production of such vaccines, to bacteria of the species *Streptococcus phocae* for use in a vaccine and to methods for combating of *Streptococcus phocae* infection in fish.

Recently in salmons, specifically Atlantic salmon (*Salmo salar*) from the Chilean coastal waters, a novel disease has been found. The disease is characterized by skin haemorrhages as petechias close to the anus, and at both sides of the fish, furuncles and lesions affecting the muscles, internal haemorrhages and congestion.

Outbreaks are acute, and often the first finding during outbreaks is an increase in mortality that can then be related to the signs mentioned above.

Outbreaks are most frequently found between mid December and mid April, mortality rising when water temperature exceeds 13.5 degrees Celsius. If an outbreak starts during the summer, it may well extend until the autumn when water temperature drops below 11 degrees Celsius.

There is no relation between the salinity of the water and outbreaks. There is no age susceptibility and post smolts to pre-harvest fish can be affected. About 4% mortality is found in December, 8% in February and 10-15% in March.

The disease has so far only been found in Atlantic salmon, and not (yet) in other salmonids such as Coho salmon or Rainbow trout.

The causative agent of the disease was however so far unknown.

It is one of the merits of the present invention that the causative agent of this disease has now been identified and moreover, that the present invention now for the first time provides a vaccine for combating the disease in fish.

It has been surprisingly found now, that the causative agent of the novel disease is a bacterium of the species *Streptococcus phocae*. This bacterium was found for the first time around 1994 when it was identified as one of the final causes of death in seals suffering from phocine distemper virus. The population of seals mostly affected by the virus comprised mainly harbor seals (*Phoca vitulina*) and grey seals (*Haliochoerus grypus*). The bacterium frequently isolated from sick seals was given the name *Streptococcus phocae* and it has been extensively characterized by Ida Skaar et al., (Int. J. of System. Bacteriol. 44: 646-650 (1994)). The so called type strain of the bacterium can be obtained from the National Collection of Type Cultures (NCTC), PHLS Central Public Health Laboratory, 61 Colindale Avenue, London NW9 5HT, United Kingdom under deposit number NCTC 12719, and from the Culture Collection of the University of Göteborg, Department of Clinical Bacteriology, Microbiologen, Guldhedsgatan 10, SE-413 46, Göteborg, Sweden under deposit number CCUG 35103.

The disease has been found in seals at many distant places, ranging from North-Eastern European countries such as England, Scotland, The Netherlands, Norway, Germany, Denmark and Sweden, to South-African seas, and in the coastal waters of parts of South America, i.a. Chile.

It was surprisingly found that this bacterium which clearly is a mammalian pathogen, could be isolated from diseased fish. This was never seen or reported, nor in Africa, nor in South-America or North-Eastern Europe or any other part of the world.

The disease in fish is so far only reported from Chile, not from North-Eastern Europe, in spite of the fact that there is extensive commercial salmon farming throughout North-Eastern Europe. Most likely, it is merely a matter of time before the disease starts affecting salmonids in other parts of the world.

It was even more surprisingly found that this bacterium seems to be a primary pathogen in fish, i.e. it is capable of causing disease in healthy fish.

Finally, it was found that this bacterium can form the basis of a vaccine for combating *Streptococcus phocae* infection.

Thus, one embodiment of the present invention relates to the use of bacteria of the species *Streptococcus phocae* for the manufacture of a vaccine for combating *Streptococcus phocae* infection in fish.

Since it has now surprisingly been found that *Streptococcus phocae* is capable of switching from mammalian species to fish species, it is most likely merely a matter of time before the bacterium infects other fish species, the first species being in the group of the salmonids.

Thus in a preferred embodiment, the bacteria of the species *Streptococcus phocae* are used for the manufacture of a vaccine for combating *Streptococcus phocae* infection in salmonids.

Since the most acute problems are currently seen in Atlantic salmons, in a more preferred embodiment the bacteria of the species *Streptococcus phocae* are used for the manufacture of a vaccine for combating *Streptococcus phocae* infection in Atlantic salmons.

The vaccine may comprise bacteria of the species *Streptococcus phocae* as a bacterin and/or in a live attenuated form. A live attenuated bacterium is a bacterium that is less pathogenic than its wild-type counterpart, while nevertheless inducing a comparable immune response. Attenuated strains can be obtained along classical routes such as chemical mutagenesis, UV-radiation and the like, or by site-directed mutagenesis.

A bacterin is defined here as bacteria of the species *Streptococcus phocae* in an inactivated form. The skilled person will notice that the method used for inactivation is not very relevant for the activity of the bacterin. Classical methods for inactivation such as UV-radiation, gamma-radiation, treatment with formalin, binary ethylene-imine, thimerosal and the like, all well-known in the art, are applicable. Inactivation of bacteria by means of physical stress, using e.g. a French Press provides an equally suitable starting material for the manufacturing of a vaccine according to the invention. A bacterin need thus not necessarily be in the form of inactivated whole cells; the cells may be disrupted.

Bacterins have the advantage over live attenuated bacteria that they are very safe. Therefore, in a preferred form, the invention relates to the use of inactivated *Streptococcus phocae* bacteria.

Vaccines as described and manufactured according to the invention can be prepared starting from a bacterial culture according to techniques well known to the skilled practitioner. Vaccines basically comprise an effective amount of a bacterium for use according to the invention and a pharmaceutically acceptable carrier. In the Example-section, examples of the preparation of a vaccine according to the invention are given. The term "effective" as used herein is defined as the amount sufficient to induce an immune response in the target fish that results in a level of pathogenesis that is less that 50% of the pathogenesis seen in fish under the same conditions, but infected with wild-type *Streptococcus phocae*.

Generally spoken, vaccines manufactured according to the invention that are based upon bacterins can be given in general in a dosage of $10^3$ to $10^{10}$, preferably $10^6$ to $10^9$, more preferably between $10^8$ and $10^9$ bacteria. A dose exceeding $10^{10}$ bacteria, although immunologically suitable, will be less attractive for economical reasons. Vaccines manufactured according to the invention that are based upon live attenuated bacteria can be given in a lower dose, due to the fact that the bacteria will continue replicating for a certain time after administration. Vaccines manufactured according to the invention that are based upon live attenuated bacteria can be given in general in a dosage of $10^2$ to $10^8$, preferably $10^3$ to $10^5$ bacteria Examples of pharmaceutically acceptable carriers that are especially suitable in a vaccine according to the invention are sterile water, saline, aqueous buffers such as PBS and the like. In addition a vaccine according to the invention may comprise other additives such as adjuvants, stabilisers, anti-oxidants and others, as described below.

Vaccines manufactured as described in the present invention may in a preferred presentation also contain an immunostimulatory substance, a so-called adjuvant. Adjuvants in general comprise substances that boost the immune response of the host in a non-specific manner. A number of different adjuvants are known in the art.

Examples of adjuvants frequently used in fish and shellfish farming are muramyldipeptides, lipopolysaccharides, several glucans and glycans and CARBOPOL(R). An extensive overview of adjuvants suitable for fish and shellfish vaccines is given in the review paper by Jan Raa (Reviews in Fisheries Science 4(3): 229-288 (1996)).

The vaccine may also comprise a so-called "vehicle". A vehicle is a compound to which the bacterium adheres, without being covalently bound to it. Such vehicles are i.a. biomicrocapsules, micro-alginates, liposomes and macrosols, all known in the art. A special form of such a vehicle, in which the antigen is partially embedded in the vehicle, is the so-called ISCOM (European Patents EP 109.942, EP 180.564, EP 242.380).

In addition, the vaccine may comprise one or more suitable surface-active compounds or emulsifiers, e.g., SPAN or TWEEN.

Oil adjuvants suitable for use in water-in-oil emulsions are e.g. mineral oils or metabolisable oils. Mineral oils are e.g. BAYOL®, MARCOL® and DRAKEOL®. Metabolisable oils are e.g. vegetable oils, such as peanut oil and soybean oil, animal oils such as the fish oils squalane and squalene, and tocopherol and its derivatives.

Suitable adjuvants are e.g. w/o emulsions, o/w emulsions and w/o/w double-emulsions Very suitable o/w emulsions are e.g. obtained starting from 5-50% w/w water phase and 95-50% w/w oil adjuvant more preferably 20-50% w/w water phase and 80-50% w/w oil adjuvant.

The amount of adjuvant added depends on the nature of the adjuvant itself, and information with respect to such amounts will be provided by the manufacturer.

Often, the vaccine is mixed with stabilisers, e.g. to protect degradation-prone proteins from being degraded, to enhance the shelf-life of the vaccine, or to improve freeze-drying efficiency. Useful stabilisers are i.a, SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

Preferably, vaccines as described are presented in a freeze-dried form.

In addition, the vaccine may be suspended in a physiologically acceptable diluent. It goes without saying, that other ways of adjuvating, adding vehicle compounds or diluents, emulsifying or stabilising a protein are also embodied in the present invention.

Many ways of administration, all known in the art can be applied. The vaccines as described are preferably administered to the fish via injection such as e.g. intraperitoneal injection, immersion, spraying, dipping or per oral. It should be kept in mind however that the route of administration may also depend on the type of vaccine: if the vaccine comprises live attenuated *Streptococcus phocae* bacteria, it could easily be administered by dipping, due to the ease of administration. If on the other hand the vaccine comprises *Streptococcus phocae* bacteria in the form of a bacterin, or more generally spoken if the vaccine can be improved by admixing an adjuvant the preferred way of administration would be the intraperitoneal route. From an immunological point of view, intraperitoneal vaccination is by far the most effective route of vaccination in fish, certainly for bacterins, especially because it allows the incorporation of adjuvants.

The administration protocol can be optimized in accordance with standard vaccination practice.

The age of the fish to be vaccinated is not critical, although clearly one would want to vaccinate against *Streptococcus phocae* infection in an early stage. For many of the vaccines for salmonids it goes that they are administered when the fish are in the pre-smolt stage and have a weight of between 15 and 35 grams. This is a very suitable moment for vaccinating against *Streptococcus phocae* as well.

For oral administration the vaccine is preferably mixed with a suitable carrier for oral administration i.e. cellulose, food or a metabolisable substance such as alpha-cellulose or different oils of vegetable or animals origin. Also an attractive method is administration of the vaccine to high concentrations of live-feed organisms, followed by feeding the live-feed organisms to the fish. Particularly preferred food carriers for oral delivery of the vaccine according to the invention are live-feed organisms which are able to encapsulate the vaccine. Suitable live-feed organisms include plankton-like non-selective filter feeders preferably members of Rotifera, *Artemia*, and the like. Highly preferred is the brine shrimp *Artemia* sp.

It would be beneficial to use, together with *Streptococcus phocae* bacteria, also one or more other fish-pathogenic bacteria or viruses, or antigens of those bacteria or viruses for the manufacture of a vaccine, which would thus be a combination-vaccine.

Examples of notorious commercially important fish pathogens are *Vibrio* species such as *Vibrio ordalii, Vibrio anguillarum* serotype O1 and *Vibrio anguillarum* serotype O2, *Aeromonas salmonicida, Flavobacterium columnarae, Tenacibaculum maritimum, Edwardsiella* species such as *Edwardsiella ictaluri* and *Edwardsiella tarda, Photobacterium damselae* subspecies *piscidida, Flavobacterium psychrophilum, Piscirickettsia salmonis, Moritella viscosa* (formerly known as *Vibrio viscosus*), *Yersinia ruckeri, Vibrio*

*salmonicida*, Infectious Pancreatic Necrotic Disease virus (EPNV), Infectious Salmon Anaemia virus (ISAV) and Salmon Pancreatic Disease virus (SPDV).

The advantage of such a combination vaccine is that it not only provides protection against *Streptococcus phocae*, but also against other diseases.

Therefore, in a preferred embodiment, the bacteria of the species *Streptococcus phocae* are used together with one or more other fish-pathogenic bacteria or viruses, or antigens of those bacteria or viruses for the manufacture of a vaccine.

In a more preferred embodiment, the fish-pathogenic bacteria or viruses, or antigens of those bacteria or viruses are selected from the group of notorious commercially important fish pathogens, as summarized above.

Merely as an example, a combination vaccine comprising (in addition to *Streptococcus phocae*) *Aeromonas salmonicida* bacteria or antigenic subunits thereof and Infectious Pancreatic Necrotic Disease virus (IPNV) as a viral antigen would protect at the same time against furunculosis, pancreatic necrosis and *Streptococcus phocae* infection. Other important viral antigens that would be useful components of such a combination vaccine are Infectious Salmon Anaemia virus (ISAV) and Salmon Pancreatic Disease virus (SPDV) or antigenic subunits of these viruses.

The viral antigen can be the whole virus or merely a subunit of the virus such as e.g. the IPN-virus VP2 protein. In this case the viral antigen is said to be derived from the whole virus.

An example of a very suitable combination vaccine is a vaccine comprising, next to *Streptococcus phocae*, also *Vibrio salmonicida* and *Aeromonas salmonicida* together with IPN-VP2. Such a vaccine provides protection against vibriosis, infectious pancreatic necrosis, furunculosis and *Streptococcus phocae* infection.

For Chile, where next to *Streptococcus phocae*, the three most common diseases in salmonid fish are a-typical furunculosis, *Piscirickettsia salmonis* (SRS) and Infectious pancreatic necrosis, a preferred vaccine would comprise in addition to the *Streptococcus phocae* vaccine component according to the invention an *Aeromonas salmonicida* component, an anti-Rickettsial component and IPN-VP2 as a viral antigen.

An otherwise highly preferred combination vaccine is a vaccine that comprises, in addition to the *Streptococcus phocae* component, at least two, but preferably more of the following species: *Vibrio anguillarum* serotype O1, *Vibrio anguillarum* serotype O2, *Aeromonas salmonicida*, *Moritella viscosa*, *Yersinia ruckeri*, *Vibrio salmonicida* and EPNV-VP2.

Another embodiment of the present invention relates to bacteria of the species *Streptococcus phocae* for use in a vaccine.

Still another embodiment of the present invention relates to methods for the production of vaccines for combating *Streptococcus phocae* infection in fish. Such methods comprise the mixing of *Streptococcus phocae* bacteria in a live attenuated or inactivated form and a pharmaceutically acceptable carrier.

A preferred form of this embodiment relates to methods that additionally comprise the mixing of an adjuvant.

Finally, an embodiment of the present invention relates to methods for the preventing and/or combating of *Streptococcus phocae* infection in fish, which methods comprise the administering to fish of an effective amount of a vaccine obtained through a method comprising the mixing of *Streptococcus phocae* bacteria in a live attenuated or inactivated form and a pharmaceutically acceptable carrier. The term "effective" as used herein is defined as the amount of a vaccine sufficient to induce an immune response in the target fish that results in a level of pathogenesis that is less that 50% of the pathogenesis seen in fish under the same conditions, but infected with wild-type *Streptococcus phocae*.

EXAMPLES

Example 1

Determination of "linking distance" of 77 Streptococcal and other Gram-positive species isolated from fish and seals on the basis of their biochemical relatedness. Amongst the strains tested are *Streptococcus phocae* isolates that were isolated from diseased salmonid fish in Chile.

| Chilean *Streptococcus* sp. trains |
|---|
| INS/AS-Code |
| AS 968 |
| INS 248 |
| AS 972 |
| AS 973 |
| AS 970 |

| Strain isolated | from | INS/AS-Code |
|---|---|---|
| February, 2001 | Atl. Salmon, 1.500 g | AS 960 |
| March, 2002 | Atl. Salmon, 2.000 g | AS 958 |
| March, 2003 | Atl. Salmon, 1.500 g | AS 959 |

These strains were isolated from different farms. Strains were isolated from spring and summer outbreaks in Atlantic salmon cultured in estuarine and marine water, resulting in high mortalities.

| Type strains obtained from Culture collections | | |
|---|---|---|
| Strain | Description | INS/AS-Code |
| CCUG 35103 | Type strain | AS 969 |
| CCUG 35104 | Ref strain | AS 971 |
| CCUG 35105 | Ref strain | AS 980 |

Strains isolated from seals suffering from pneumonia by, and obtained from, Ida Skaar Norway, (Aug. 18, 2003), described in: Skaar et al., 1994 (See above):

| Strain | Description | INS Code |
|---|---|---|
| 7908 | P2 | AS 974 |
| 8026 | L2 | AS 975 |
| 8056 | P2 | AS 976 |
| 8059 | P2 | AS 977 |
| 8205 | H2 | AS 978 |
| 8252 |  | AS 979 |

Identification

All strains, (Chile-strains, *S. phocae* type and reference strains and remaining non-deposited strains from Norway) were identified in 46 phenotypic and morphological tests (Gram-reaction, Catalase-reaction, Oxidase-reaction, haemolysis, growth on 40% bile salts, Gelatinase-production, API(API 20 Strep test kit BioMerieux), Oxidation/Fermentation test (w & w/o oil), Kligler Triple Sugar reactions (Lactose, Glucose, gas-production, $H_2S$ production), fermentation of Amygdalin, Galactose, Glycerol, Maltose, Melibiose, Melizitose, Sucrose, Nitrate, growth at pH9.6, in 6.5% salt, 3% salt tolerance, indol-production and motility).

The identification profiles obtained were incorporated in an existing data matrix containing fish pathogenic Gram-positive bacterial species (*Streptococcus agalactiae, S. difficile, S. iniae, Carnobacterium piscicola, Vagocossus salmoninarum, Nocardia seriolae* and *Lactococcus garvieae*) as well as reference strains of *S. mutans, S. zooepidermicus* and *S. equi*, and similarities were computed using UPGMA analysis. The results of this phylogenetic tree analysis are represented in the dendrogram in FIG. 1. All strains in the row between and including INS 248 and AS 958 belong to the same cluster, i.e. they belong to the species *S. phocae*.

Based on phenotypic and morphological testing the strains isolated from Chile are indistinguishable from the strains originally isolated from seals with, pneumonia in Norway.

Conclusion: the bacterial strains isolated from Atlantic salmon in Chile as the causative agent of Streptococcal disease were identified on the basis of their biochemical relatedness as *Streptococcus phocae*.

Example 2

Determination of phylogenetic distance of *S. phocae* strains and other streptococcal strains on the basis of 16 S rRNA sequence analysis. A 16 rRNA sequence analysis has been performed on the *Streptococcus phocae* type reference strain NCTC 12719 and two *Streptococcus phocae* isolates (AS 972 and AS 973) that were isolated from diseased salmonid fish in Chile. A comparison was made between the *S. phocae* type strain, the two Chilean isolates and several members of other *Streptococcus species*: *S. dysgalactiae, S. iniae* and *S. agalactiae*.

16S rRNA sequences were determined as described by Kuhnert et al., (Int. J. Syst. Bacteriol., 46;1174-1176 (1996)). For both strains, a sequence of approximately 1410 nt was obtained. These sequences were compared with available nucleotide sequence databases, using the BLAST N software. The highest scoring sequences were aligned using CLUSTAL X in the VECTOR NTI software package (Informax Inc.) with the following settings: a gap opening penalty of 15 and a gap extension penalty of 6.66, both for pair wise and multiple alignments. For the construction of the tree the Neighbor-Joining method by Saitou, N. and Nei, M. was used. (The neighbor-joining method: a new method for reconstructing phylogenetic trees. Mol. Biol. Evol. 4, 406-425 (1987)). Positions with gaps were excluded from analysis.

Figure 2:
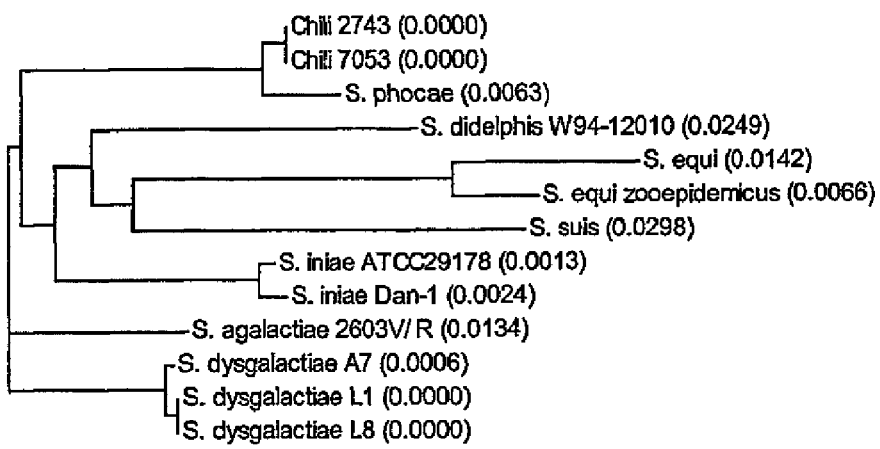

The phylogenetic tree indicating the relatedness of the various Streptococcal strains is given in FIG. 2.

Conclusion: as is clear at first sight from FIG. 2, the Chilean isolates AS 972 and AS 973 are in the same branch as the *S. phocae* type strain. This is fully in line with the outcome and conclusions of the phylogenetic tree of FIG. 1, which represents the biochemical relatedness of the various *S. phocae* isolates from seals and fish.

Example 3

Safety Trial and Seroconversion in Asian Sea Bass (*Lates calcarifer*)

It was decided to first test the safety and seroconversion of *S. phocae* vaccines in a fish species that is not susceptible to *S. phocae*.
Vaccine Preparation:
A crude vaccine was prepared by growing strain AS 972 for 22.5 hours in SGM 5× glucose medium on an orbital shaker (129 RPM) at 32° C. After incubation the total count obtained was $2.9 \times 10^9$ cells/ml. The culture was inactivated with 0.5% formalin and subsequently concentrated by centrifugation to a final concentration of $1.5 \times 10^{10}$ cells/ml. Bacterial cells were resuspended in culture supernatant.
Vaccination:
A total of 56 fish (Asian Sea bass) were injected intraperitoneal (IP) with 0.1 ml the above vaccine whereas 55 fish were injected with PBS. The latter group served as control. The mean weight of the vaccinated and control fish at the start of the experiment was 19.7 and 20.1 grams respectively.

No mortality occurred immediately after the vaccination. Vaccinated and control fish were kept in the same tank, separated by means of a vertical separation net placed in the middle of the tank.
Safety Evaluation:
Fish were monitored for a total of 21 days after the vaccination. No mortality occurred during this period in neither the control or the vaccinated group. The mean fish weight at the end of the observation period for vaccinated and control fish was 25.7 and 25.0 grams respectively. It can be concluded that the vaccine prepared was safe for Asian Sea bass.
Pathogenicity Evaluation:
A challenge model was evaluated by IP-injection of live *Streptococcus phocae* strains AS 972/AS 960 ($5 \times 10^4$, $5 \times 10^6$ and $5 \times 10^7$ CFU/fish).

No mortality could be obtained with any of the bacterial concentrations/strains tested: it was found that Sea bass is not susceptible to *S. phocae* infection. Therefore, the efficacy of the vaccines could not be evaluated in Asian Sea bass.
Seroconversion:
As follows directly from the tables in FIG. 3, seroconversion obtained three weeks after first vaccination with a water-based vaccine is already about 80% of the seroconversion found three weeks after challenge with live *Streptococcus phocae*. Booster vaccination, at three weeks after first vaccination, with a water-based vaccine gave a titer equal to that after challenge. Booster vaccination, at three weeks after first vaccination, with an water/oil emulsion-based vaccine gave a titer that is slightly lower than the first vaccination to that after challenge. This is a normal effect seen in general with water/oil emulsion-based vaccines; the effect of boosting will be seen after a longer time period compared to water-based vaccines.

Seroconversion was determined as follows:
*Streptococcus phocae* was coated overnight to NUNC MAX-ISORB at $10^7$ bacteria/well. ELISA was developed using a mouse monoclonal antibody directed against the light chain of European Sea bass IgM (cross-reactive with Asian Sea bass IgM), followed by incubation with peroxidase conjugated goat-anti-mouse antibodies. Titers are expressed as $OD_{450}$ reading.

Conclusion: even a single vaccination is already capable of inducing antibody-titers that are close to those found in challenged fish, whereas a booster vaccination gives an antibody-titer that is equal to those found in challenged fish.

Example 4

Safety Trial and Seroconversion in Atlantic Salmon

Vaccine Preparation:
Vaccines were prepared as described in Example 3
Vaccination:
A total of 250 fish (Atlantic salmon) were injected intraperitoneal (IP) with 0.1 ml the above vaccine whereas 130 fish were injected with PBS. The latter group served as control. The mean weight of the vaccinated and control fish at the start of the experiment was 28 grams.

No mortality occurred immediately after the vaccination. Vaccinated and control fish were marked by Panjet labeling and kept in the same tank.

Safety Evaluation:

Fish were monitored for a total of 42 days after the vaccination. No mortality occurred during this period in neither the control or the vaccinated group. No abnormal behavior has been seen. It can be concluded that the vaccine is safe for Atlantic salmon.

Challenge will be done with $1.5 \times 10^9$ CFU of live *Streptococcus phocae*/fish.

Seroconversion:

Formalin inactivated Streptococcus phocae Strain INS 972 was diluted in coating buffer to $10^7$ bacteria/ml. Subsequently 0,1 ml was added to individual wells of 96 wells NUNC MAXISORB plates, incubated over night at 2-8° C. and washed three times. Wells were then incubated with serial dilutions of salmon sera. Subsequently the bound antibodies were quantified using rabbit-anti-salmon, HR-peroxidase-conjugated goat-anti-rabbit IgG and peroxidase substrate. Titers are expressed $OD_{492}$ reading.

As follows directly from FIG. 4, vaccination with a water-based vaccine gives a relative increase in titer of 500% after six weeks, whereas a w/o-emulsion based vaccine gives a relative increase in titer of 200%.

Conclusion: a single vaccination with a water-based vaccine was able to increase the antibody level with approx. 500% compared to saline injected control group, 6 weeks post vaccination. When using a water/oil emulsion-based vaccine in the same vaccination regime, a delayed onset was observed resulting in a increase of antibody level with approx. 200% compared to saline injected control group

LEGEND TO THE FIGURES

FIG. 1: phylogenetic tree of 77 Streptococcal and other Gram-positive species isolated from fish and seals on the basis of their biochemical relatedness.

FIG. 2: phylogenetic tree of *S. phocae* strains (reference strain NCTC 12719 and two Chilean *Streptococcus phocae* isolates from fish) and other streptococcal strains on the basis of 16 S rRNA sequence analysis.

Figure 3:
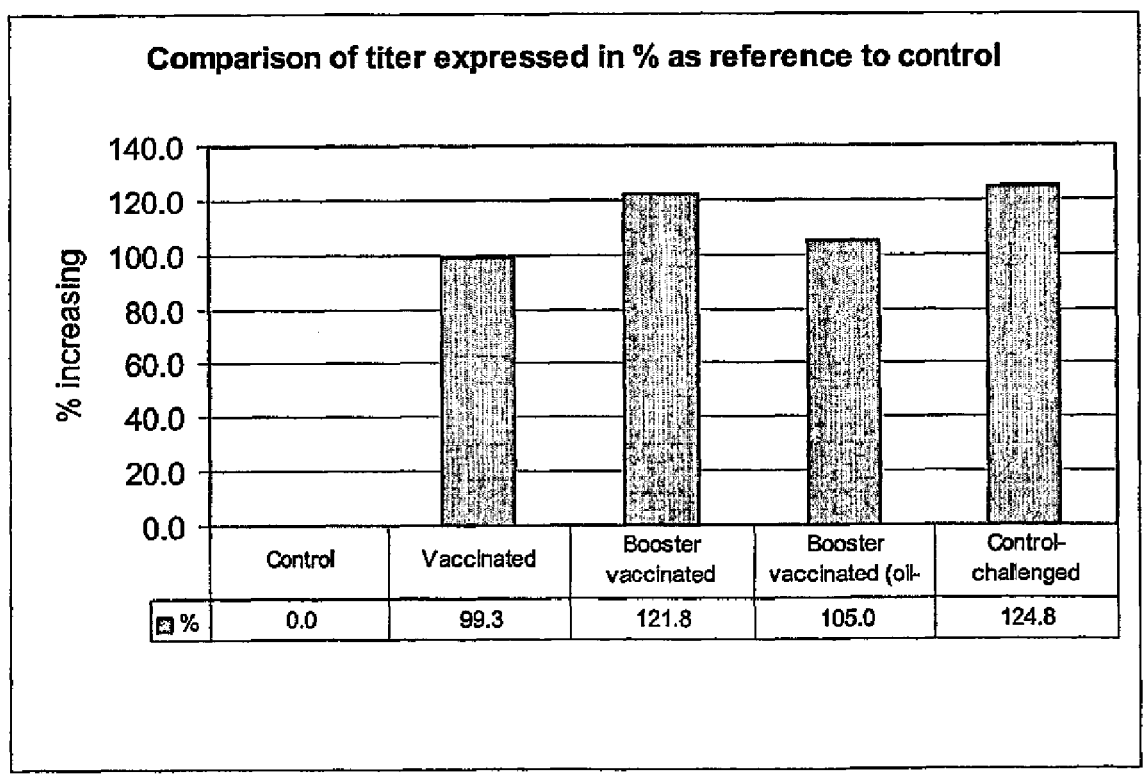

FIG. 3: ELISA determination after vaccination/challenge of *S. phocae* in Sea bass.

Figure 4:
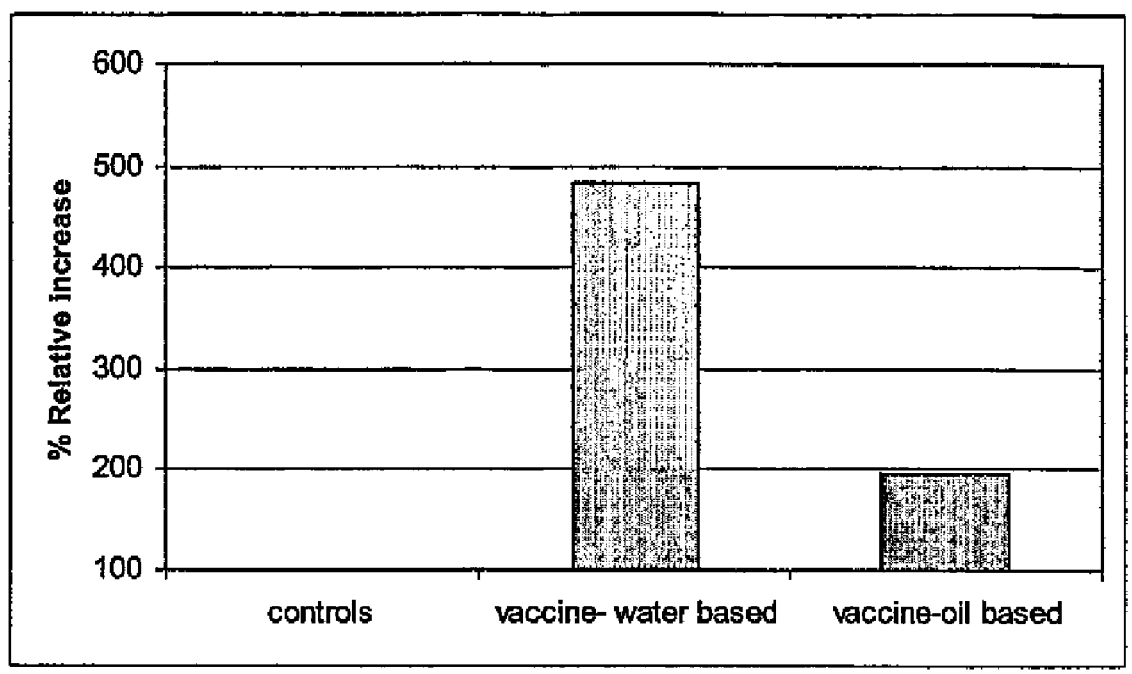

FIG. 4: ELISA determination after vaccination/challenge of *S. phocae* in Atlantic salmon.

The invention claimed is:

1. A method for inducing an immune response in fish comprising administering an immunogenic composition to fish, wherein the immunogenic composition comprises an immunogenically effective amount of a bacterium of the species *Streptoccus phocae*.

2. The method according to claim 1, wherein the fish are salmonids.

3. The method according to claim 2, wherein the fish are Atlantic salmon.

4. The method according to claim 1, wherein the bacterium is in an inactivated form.

5. The method according to claim 1, wherein said immunogenic composition comprising *Streptococcus phocae* further comprises at least one additional immunogen selected from the group consisting of
   i) an additional fish-pathogenic microorganism,
   ii) a fish-pathogenic virus, and
   iii) an antigen of (i) or (ii).

6. The method according to claim 5, wherein the at least one additional immunogen is a fish-pathogenic microorganism or virus selected from the group consisting of *Vibrio ordalii*, *Vibrio anguillarum* serotype O1, *Vibrio anguillarum* serotype O2, *Aeromonas salmonicida*, *Flavobacterium columnarae*, *Flexibacter maritimus*, *Edwardsiella ictaluri*, *Edwardsiella tarda*, *Photobacterium damselae* subspecies *piscidida*, *Flavobacterium psychrophilum*, *Moritella viscosa*, *Piscirickettsia salmonis*, *Yersinia ruckeri*, *Vibrio salmonicida*, Infectious Pancreatic Necrotic Disease virus, Infectious Salmon Anaemia virus and Salmon Pancreatic Disease virus.

7. The method according to claim 1, wherein the immunogenic composition further comprises an adjuvant.

8. The method of claim 1, wherein said immunogenic composition comprises a pharmaceutically acceptable carrier.

* * * * *